(12) United States Patent
Tavger

(10) Patent No.: US 10,149,970 B2
(45) Date of Patent: Dec. 11, 2018

(54) METHOD AND SYSTEM FOR DELIVERING SOLUTION INTO THE PORES OF RECIPIENT HUMAN SKIN

(71) Applicant: Michael Tavger, Katzrin (IL)

(72) Inventor: Michael Tavger, Katzrin (IL)

( * ) Notice: Subject to any disclaimer, the term of this patent is extended or adjusted under 35 U.S.C. 154(b) by 835 days.

(21) Appl. No.: 14/479,321

(22) Filed: Sep. 7, 2014

(65) Prior Publication Data

US 2014/0378889 A1    Dec. 25, 2014

Related U.S. Application Data

(63) Continuation-in-part of application No. PCT/IL2013/050369, filed on May 2, 2013.

(30) Foreign Application Priority Data

Jun. 18, 2012    (IL) .......................................... 220486

(51) Int. Cl.
    *A61M 37/00*    (2006.01)
    *A61M 35/00*    (2006.01)
    (Continued)

(52) U.S. Cl.
    CPC ......... *A61M 37/0092* (2013.01); *A45D 34/04* (2013.01); *A61M 35/003* (2013.01);
    (Continued)

(58) Field of Classification Search
    CPC . A61M 37/00; A61M 35/003; A61M 37/0092
    See application file for complete search history.

(56) References Cited

U.S. PATENT DOCUMENTS 3,994,300 A * 11/1976 Siddons ................. A61B 18/14
                                                    219/223
4,140,121 A *  2/1979 Kuhl .................... A61M 5/14276
                                                    424/423
(Continued)

FOREIGN PATENT DOCUMENTS

WO    WO 2006/086742    8/2006
WO    WO 2011/043736    4/2011

OTHER PUBLICATIONS

Flament et al. Facial skin pores: a multiethnic study; 2015:8, pp. 85-93.*

(Continued)

*Primary Examiner* — Bhisma Mehta
*Assistant Examiner* — Matthew A Engel
(74) *Attorney, Agent, or Firm* — Alphapatent Associates, Ltd; Daniel J. Swirsky

(57) ABSTRACT

A method for delivering liquid into the pores of recipient human skin is provided. The method comprises delivering, via a nozzle, at least one stream of the liquid under pressure to the pores, the stream having a cross-section with a diameter no greater than about 50 μm, applying a negative pressure across an area of the skin being treated, rotating the nozzle relative to the area at a speed up to about 200 revolutions per minute, contacting an electrode connected to a first terminal of a power source, having a first electric charge, to the skin, and contacting a second terminal of the power source, having a second electric charge, opposite the first electric charge, to the liquid, thereby imparting an electrical current between about 0.2 mA and 0.3 mA to the skin in the vicinity of the pores. The delivering, applying, rotating, and contactings occur simultaneously.

5 Claims, 5 Drawing Sheets

(51) Int. Cl.
*A61M 5/42* (2006.01)
*A61M 5/30* (2006.01)
*A45D 34/04* (2006.01)

(52) U.S. Cl.
CPC .............. *A61M 5/30* (2013.01); *A61M 5/3007* (2013.01); *A61M 5/425* (2013.01)

(56) References Cited

U.S. PATENT DOCUMENTS

| | | | |
|---|---|---|---|
| 4,498,474 A * | 2/1985 | Chalmers | A61B 18/14 606/36 |
| 4,549,854 A * | 10/1985 | Yamamoto | B65G 47/911 294/64.2 |
| 5,226,907 A * | 7/1993 | Tankovich | A45D 26/00 606/131 |
| 5,380,272 A * | 1/1995 | Gross | A61N 1/0448 604/20 |
| 5,421,816 A * | 6/1995 | Lipkovker | A61M 37/0092 604/20 |
| 5,522,814 A * | 6/1996 | Bernaz | A61B 18/14 606/36 |
| 5,562,643 A * | 10/1996 | Johnson | A61M 37/00 604/236 |
| 5,752,948 A * | 5/1998 | Tankovich | A61B 18/1442 606/133 |
| 5,827,235 A | 10/1998 | Beaver | |
| 5,871,480 A * | 2/1999 | Tankovich | A45D 26/00 606/131 |
| 5,913,833 A * | 6/1999 | Elstrom | A61B 5/14514 600/573 |
| 5,947,928 A | 9/1999 | Muller | |
| 6,022,316 A * | 2/2000 | Eppstein | A61N 1/0416 600/309 |
| 6,074,385 A * | 6/2000 | Klopotek | A61B 18/14 128/898 |
| 6,267,771 B1 * | 7/2001 | Tankovich | A45D 26/00 128/898 |
| 6,283,936 B1 * | 9/2001 | Tavger | A61B 17/545 604/24 |
| 6,508,813 B1 * | 1/2003 | Altshuler | A61B 18/203 606/16 |
| 6,527,716 B1 * | 3/2003 | Eppstein | A61B 1/313 600/309 |
| 6,607,508 B2 | 8/2003 | Knauer | |
| 6,652,483 B2 | 11/2003 | Slate et al. | |
| 6,678,554 B1 * | 1/2004 | Sun | A61N 1/325 604/20 |
| 6,846,306 B1 * | 1/2005 | Haas | C12M 35/02 435/285.2 |
| 7,025,774 B2 | 4/2006 | Freeman et al. | |
| 7,226,439 B2 | 6/2007 | Prausnitz et al. | |
| 7,315,758 B2 | 1/2008 | Kwiatkowski et al. | |
| 7,329,252 B1 * | 2/2008 | Yamazaki | A61B 18/203 606/10 |
| 8,814,836 B2 * | 8/2014 | Ignon | A61B 17/54 604/289 |
| 9,056,193 B2 * | 6/2015 | Ignon | A61M 35/003 |
| 9,468,464 B2 * | 10/2016 | Shadduck | A61B 17/54 |
| 9,474,886 B2 * | 10/2016 | Ignon | A61B 17/545 |
| 2002/0016601 A1 * | 2/2002 | Shadduck | A61B 17/50 606/131 |
| 2002/0133149 A1 * | 9/2002 | Bessette | A61B 18/14 606/41 |
| 2002/0138037 A1 * | 9/2002 | Weimann | A61M 37/0092 604/22 |
| 2002/0147466 A1 * | 10/2002 | Bernabei | A61H 7/008 607/3 |
| 2002/0169394 A1 * | 11/2002 | Eppstein | A61B 5/00 600/573 |
| 2003/0187478 A1 * | 10/2003 | Bernabei | A61H 7/008 607/3 |
| 2005/0049542 A1 * | 3/2005 | Sigg | A61N 1/327 604/20 |
| 2006/0052739 A1 * | 3/2006 | Henley | A61N 1/0428 604/20 |
| 2008/0208104 A1 * | 8/2008 | Bragagna | A61B 18/203 604/20 |
| 2008/0319453 A1 * | 12/2008 | Tavger | A61B 17/545 606/131 |
| 2009/0036824 A1 * | 2/2009 | Tavger | A61M 5/30 604/24 |
| 2009/0222023 A1 * | 9/2009 | Boone, III | A61B 17/545 606/131 |
| 2009/0234269 A1 * | 9/2009 | Tavger | A61M 11/02 604/20 |
| 2010/0180738 A1 * | 7/2010 | Tavger | B24C 1/045 83/53 |
| 2010/0305495 A1 | 12/2010 | Anderson et al. | |
| 2011/0224691 A1 * | 9/2011 | Whyte | A61B 17/3203 606/131 |
| 2012/0259266 A1 * | 10/2012 | Quisenberry | A61F 7/02 604/20 |
| 2014/0378889 A1 * | 12/2014 | Tavger | A61M 35/003 604/20 |
| 2015/0231379 A1 * | 8/2015 | Ignon | A61M 35/003 604/22 |
| 2016/0089525 A1 * | 3/2016 | Grez | A61B 17/54 604/20 |
| 2018/0099140 A1 * | 4/2018 | Tavger | A61N 1/303 |

OTHER PUBLICATIONS

L. M. Harding, et al, "Comparison of a Needle-Free High-Pressure Injection System with Needle-Tipped Injection of Intracavernosal Alprostadil for Erectile Dysfunction", International Journal of Impotence Research (2002) 14, 498-501.

\* cited by examiner

METHOD AND SYSTEM FOR DELIVERING SOLUTION INTO THE PORES OF RECIPIENT HUMAN SKIN

CROSS-REFERENCE TO RELATED APPLICATIONS

This application is a Continuation-In-Part of International Patent Application No. PCT/IL2013/050369, filed May 2, 2013, which claims the benefit of priority from Israel Patent Application No. 220486, filed Jun. 18, 2012, the contents of which are incorporated by reference in their entirety.

FIELD OF THE INVENTION

This invention relates to the delivery system and method for delivery of solutions into the human skin via pores.

BACKGROUND OF THE INVENTION

Improvement of the appearance of the skin and slowing down its aging process is achieved using different procedures and technologies. The effect of supplements to eliminate wrinkles, pigmentation unevenness, sun damage and protect the skin from environmental hazards is based on their penetration through the skin. The main obstacle for the penetration of supplements through the skin is the stratum corneum which is only about 50-200 µm thickness. This thin barrier prevents passage of any substance whose size is bigger than a water molecule.

U.S. Pat. Nos. 6,607,508 and 7,025,774 disclose devices and methods for drug delivery by injection, wherein the skin is punctured by a needle and medicine is injected to the required depth. Injections allow for flexible local treatment, direct absorption of the solutions and their delivery to the intercellular fluids by using a minimal substance amount. Disadvantages of such an approach are the sophisticated technique required, the risk of infection, cross-contamination, pain, difficulty of injection depth control, and the danger of harming blood vessels. Another syringe type, the so-called needle-free injector, has the additional drawback that it does not allow for adequate control of the drug injection depth. Such devices are described in "*Comparison of a needle free high-pressure injection system with needle-tipped injection of intracavernosal alprostadil for erectile dysfunction*", L. M. Harding, A. Adeniyi, R. Everson, S. Barker, D. J. Ralph and A. P. Baranowski, in International Journal of Impotence Research (2002) 14, 498-501.

U.S. Pat. Nos. 6,652,483, 5,947,928 and 7,226,439 disclose methods and devices for transdermal medicine delivery into the skin. The delivery is controlled by the solutions' physical and chemical parameters: diffusion, solubility and affinity. Diffusion depends on the molecule size. As molecule size decreases, permeability improves. U.S. Pat. No. 7,315,758 proposes additional physical means to increase diffusion, for example, electrical, magnetic and sonar. Transportation of hydrophilic or charged molecules is a particularly difficult process because of the low water content in the stratum corneum which is lipids-based: the skin (epidermis) layer is composed of about 40% lipids, 40% protein and only 20% water. This makes the diffusion method of medicine delivery slow and inefficient.

Delivery of cosmetic and medical solutions via pores could possibly be efficient since pores cover the majority of the skin surface. The pores enable water transfer vital for thermoregulation and for the transfer of the products of metabolism only from the dermis to the surface and not vice versa. These channels contain structured hydrophilic and lipophilic domains that feature exclusively unilateral conductivity toward the outside.

A square millimeter of skin surface contains not less than 3 pores. Pore size depends on pore condition and activity. On average, pore diameter is from 50 to 300 µm. Pores are tubular twisting capillaries that arrive from the depth of the dermis and gradually become cylindrical tubes that open onto the surface of the stratum corneum. The total surface area of pores is less than 1% (0.1% to 1%) of the entire surface area of the skin; hence pores cannot facilitate the delivery of a sufficient amount of material through diffusion. The inventor is not acquainted with methods and devices for delivery of cosmetic and medical solutions via pores that are not based on molecular diffusion.

The delivery of medical or cosmetic solutions through the skin would be facilitated if it were possible to inject solutions directly into the pores.

SUMMARY OF THE INVENTION

It is therefore an object of the invention to facilitate the delivery of solutions through the skin by injection directly into the pores.

This object is realized according to the invention by a method and system having the features of the respective independent claims herein.

Human skin has at least three types of pores, i.e., hair follicles, sebaceous glands and sweat glands. The proposed method of delivery of cosmetic and medical material exploits the fact that these skin appendages bypass stratum corneum defense and provide access to the dermis. The modality of the method is that the device for medical solution delivery has a tip with one or more nozzles that are smaller than pore size. Negative pressure is applied in order to ensure that the outlets of the device nozzles coincide with the inlets of the pores. In order to deliver the material through a larger number of pores on the treated skin surface, the device is shifted relative to the pores.

Since the outlet diameter of the nozzle is smaller than the size of a pore opening, the pressure of the jet superposed with the pore does not meet any skin resistance and does not cause skin damage in the flow direction. The negative pressure causes the treated skin area to adjoin the inner surface of the nozzle tip. As the device is shifted over the skin surface the nozzle orifices and the pore inlets become connected for short periods of superposition and the pore channel is filled with the medicine or cosmetic. As a result of filling, the pore inlet is widened and filled with even more medicine or cosmetic. If the orifice of the nozzle were larger than that of the pore inlet, the jet pressure would also affect the skin region surrounding the pore, causing compressive deformation of the skin inward and consequently closing the pore and preventing the medicine or cosmetic from permeating into the skin. Moving the device over the skin surface allows for skin treatment by means of medical or cosmetic solution delivery to a large number of pores.

A device implementing the proposed method of medicine or cosmetic solution delivery into the human skin consists of a compressor, ejector, separation container (separator), container for medical or cosmetic solution storage, pumping unit, operational handpiece with a port for the solution supply under pressure and waste evacuating port.

Although pores occupy only a small portion of the entire skin surface, the total surface area of the interiors of the pores on the skin can be as much as about 6 times greater than the rest of the epidermis surface. As the interior of the pores do not have exposure to sunlight and contact with atmospheric oxygen, epidermal coverage thereof is not strong. The presently disclosed subject matter may be used to facilitate the use of the macro-structure of the pores for transportation of medical or cosmetic solutions to a uniform depth over the treated skin surface.

According to one aspect of the presently disclosed subject matter, there is provided a method for delivering liquid into the pores of recipient human skin, the method comprising:

delivering, via a nozzle, at least one stream of the liquid under pressure to the pores, the stream having a cross-section with a diameter no greater than about 50 μm;

applying a negative pressure across an area of the skin being treated;

rotating the nozzle relative to the area at a speed up to about 200 revolutions per minute;

contacting an electrode connected to a first terminal of a power source, having a first electric charge, to the skin; and contacting a second terminal of the power source, having a second electric charge, opposite the first electric charge, to the liquid, thereby imparting an electrical current between about 0.2 mA and 0.3 mA to the skin in the vicinity of the pores;

wherein the delivering, applying, rotating, and contactings (i.e., the contacting of the first and second terminals of the power source) occur simultaneously.

The first electric charge may be a positive charge, with the second electric charge being a negative charge.

The liquid may comprise a medical or cosmetic solution.

According to another aspect of the presently disclosed subject matter, there is provided a method for delivering liquid into the pores of recipient human skin, the method comprising:

delivering at least one stream of the liquid under pressure to the pores, the stream having a cross-section at its widest point smaller than an inlet opening of the pore;

contacting an electrode connected to a first terminal of a power source, having a first electric charge, to the skin; and contacting a second terminal of the power source, having a second electric charge, opposite the first electric charge, to the liquid, thereby imparting an electrical current between about 0.2 mA and 0.3 mA to the skin in the vicinity of the pores;

wherein the delivering and contacts occur simultaneously.

The electrical current may be between about 0.2 mA and 0.3 mA.

The diameter of the cross-section of the stream may be no greater than about 50 μm.

The first electric charge may be a positive charge, with the second electric charge being a negative charge.

The method may further comprise applying, simultaneously with the delivering and contactings, negative pressure across an area of skin being treated.

The liquid stream may be delivered via a nozzle, the method further comprising moving the nozzle relative to the area.

The nozzle may comprise rotating the at least one nozzle.

The nozzle may be rotated at a speed up to about 200 revolutions per minute.

The liquid may comprise a medical and/or cosmetic solution.

According to a further aspect of the presently disclosed subject matter, there is provided a system for delivering a liquid, which may comprise a medical or cosmetic solution, into pores of a human's skin, the system comprising:

a storage container for containing the liquid;

a pumping unit coupled to the storage container for increasing the pressure of the liquid;

a suction mechanism configured to generate a negative pressure;

a power source having first and second terminals of opposite charges;

an electrode connected to the first terminal of the power source and being configured for being brought into contact with the skin during the delivery; and a handpiece with a tip having at least one nozzle for delivery of the liquid into pores of the human skin wherein the nozzle delivers a stream having a cross-section at its widest point smaller than an inlet of the pore, the handpiece being configured to bring the liquid into contact with the second terminal of the power source, thereby facilitating imparting an electrical current to the skin in the vicinity of the pores.

The electrical current may be between about 0.2 mA and 0.3 mA.

The diameter of the cross-section of the stream may be no greater than about 50 μm.

The first electric charge may be a negative charge, with the second electric charge being a positive charge.

The tip may be configured to rotate, for example at a speed up to about 200 revolutions per minute.

The suction mechanism may comprise a compressor and a gas ejector.

The handpiece may comprise a vacuum port connected to a vacuum unit configured for applying negative pressure via the tip of the handpiece across an area of skin being treated.

According to a further aspect of the presently disclosed subject matter, there is provided a system for delivering a liquid, which may comprise a medical or cosmetic solution, into pores of a human's skin, the system comprising:

a pumping unit coupled to the storage container for increasing the pressure of the liquid;

a power source having first and second terminals of opposite charges;

an electrode connected to the first terminal of the power source and being configured for being brought into contact with the skin during the delivery.

a handpiece comprising a tip having at least one nozzle for delivery of the liquid into pores of the human skin wherein the nozzle delivers a stream having a cross-section with a diameter no greater than about 50 μm, the handpiece being configured to bring the liquid into contact with the second terminal of the power source, thereby facilitating imparting an electrical current between about 0.2 mA and 0.3 mA to the skin in the vicinity of the pores, the tip being configured to rotate at a speed up to about 200 revolutions per minute; and a suction mechanism configured to generate a negative pressure via the tip.

The first electric charge may be a negative charge, with the second electric charge being a positive charge.

The suction mechanism may comprise a compressor and a gas ejector.

The suction mechanism may comprise a vacuum port configured to be connected to a vacuum unit.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF THE INVENTION

Figure 1A:
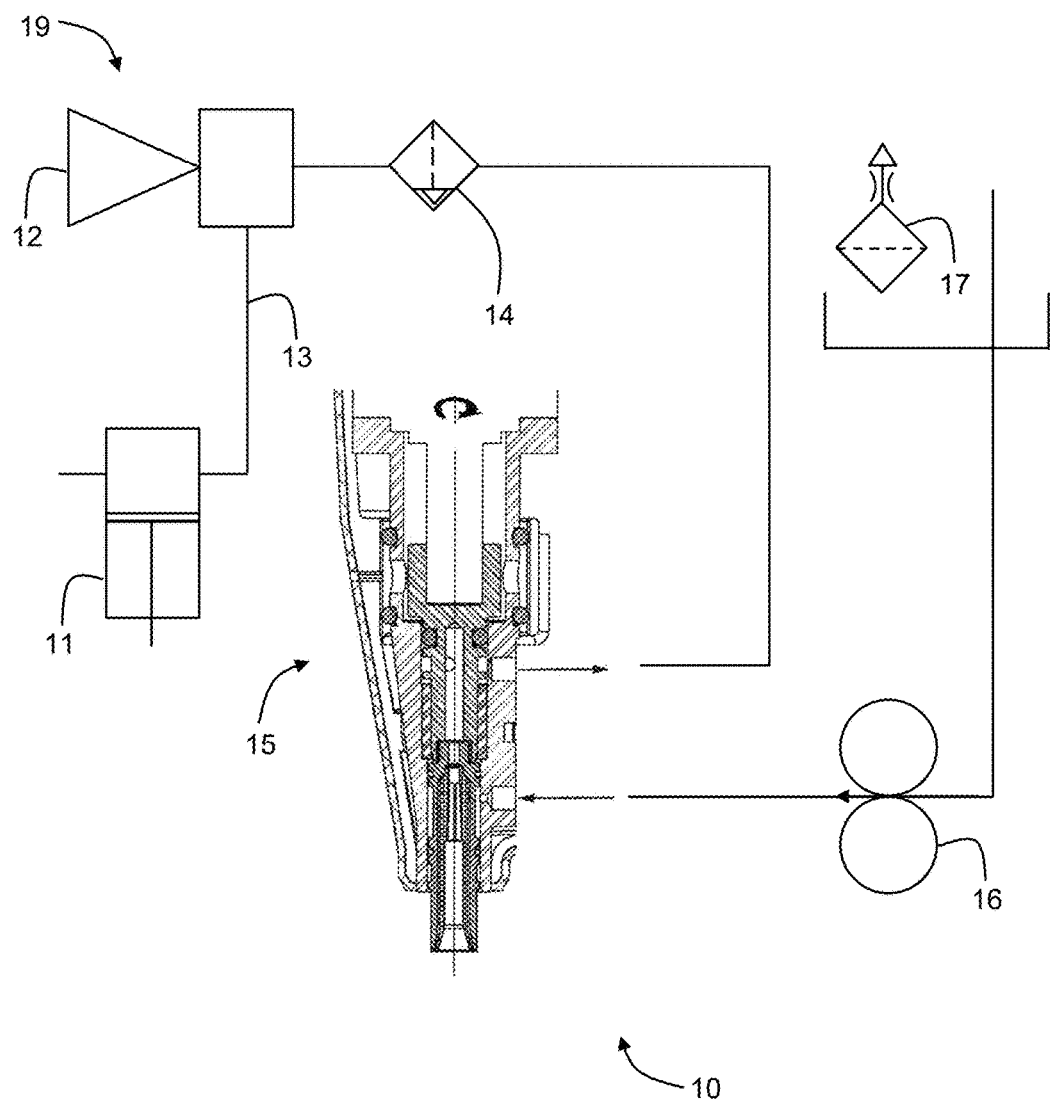
FIG. 1a illustrates one example of a system for the delivery of a medical or cosmetic solution to the skin via pores.

Referring to FIG. 1a, there is shown one example of a system 10 comprising suction mechanism, which is generally indicated at 19, connected to a separation container 14 which is connected to an operating handpiece 15. The handpiece 15 is connected to a pumping unit 16 which is in turn connected to a storage container 17 for storing a liquid such as a medical or cosmetic solution. According to some examples, for example as indicated in FIG. 1a, the suction mechanism may comprise a compressor 11 connected to a gas ejector 12 (which is connected to the separation container 14) by a tube 13. According to other examples (not illustrated), the suction mechanism 19 comprises a vacuum pump or any other suitable arrangement, connected to a vacuum port (not illustrated) in the handpiece 15.

The compressor 11 is used for the air compression needed to generate negative pressure in the gas ejector 12. The gas ejector 12 does not contain moving parts, which makes it preferable for negative pressure generation in humid media. The separation container 14 provides liquid separation of the liquid-gas mixture. The storage container 17 is used for solution storage and its delivery to the pumping unit 16, which provides the high pressure used for the solution delivery.

Figure 1B:
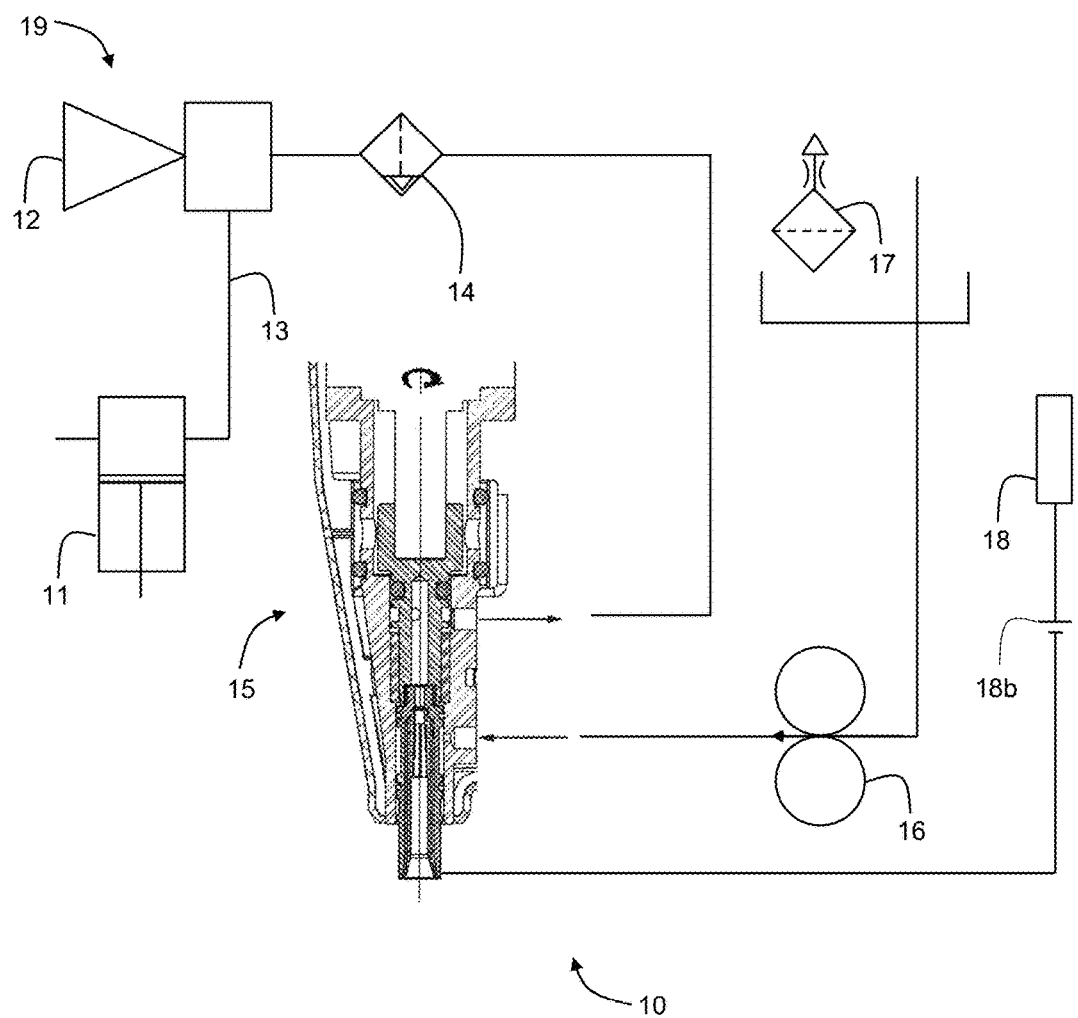
FIG. 1b illustrates another example of a system for the delivery of a medical or cosmetic solution to the skin via pores.

FIG. 1b illustrates another example of a system 110, which is a modification of the system 10 illustrated in FIG. 1a. The system 110 comprises the same components as described above with reference to the system illustrated in FIG. 1a, and operates similarly thereto. In addition, the system 110 illustrated in FIG. 1b comprises an electrode 18. The electrode is connected to one terminal (i.e., either positive or negative) or a power source 18b, which may be any suitable source of electrical power. The other terminal (having the opposite charge) of the power source is connected to part of the handpiece 15 with which the liquid therein comes into contact, such as the tip 23 (described below). The electrode 18 is designed to contact a patient's skin during use, for example by being grasped thereby or by being clasped/fastened thereto. Thus, the patient completes a circuit between the two terminals of the power source 18b, facilitating an electrical current from being imparted to his skin in general, and in the vicinity of the pores in particular.

It will be appreciated that while the present disclosure describes, by way of non-limiting example only, that the electrode connects the user's skin to the positive terminal of the power source 18b, and the handpiece 15 connects the liquid to the negative terminal of the power source, the reverse may be the case, i.e., the electrode may connect the user's skin to the negative terminal of the power source, while a the handpiece connects the liquid to the positive terminal of the power source.

Figure 2:
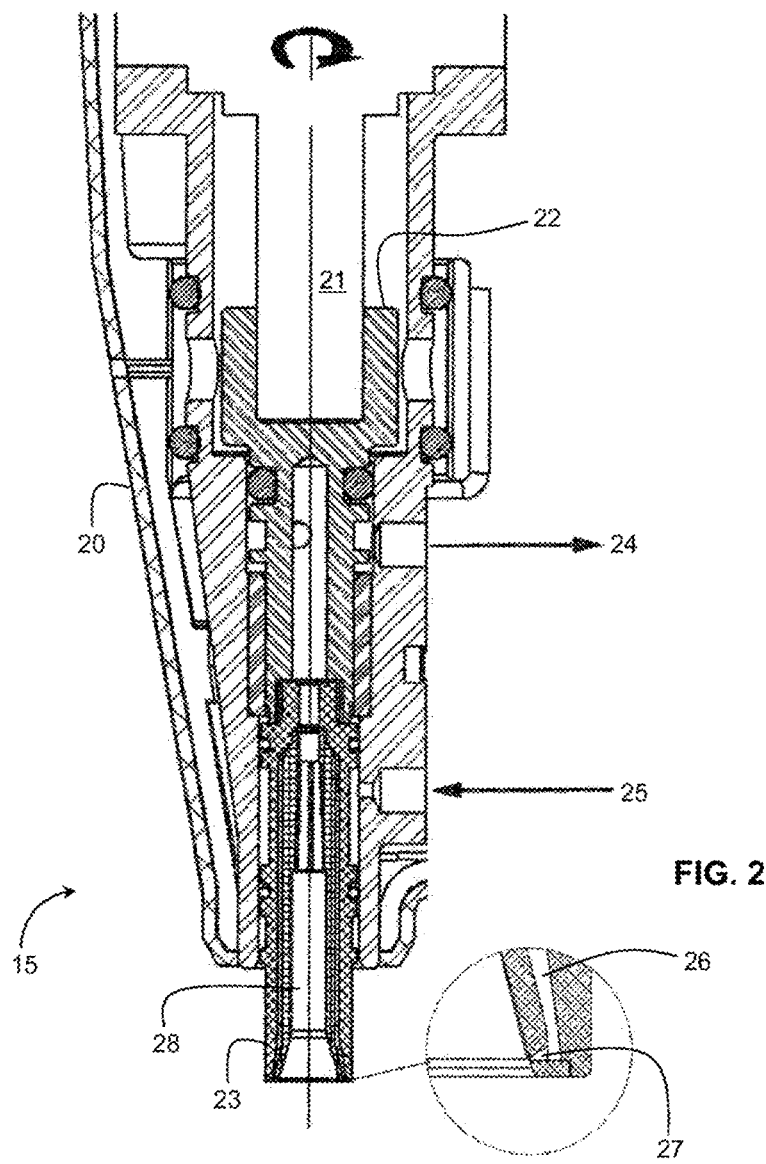
FIG. 2 is a partial section of an operational handpiece for use in the system shown in FIG. 1.

FIG. 2 shows in enlarged scale that the operating handpiece 15 includes an outer casing 20 accommodating a motor 21, which is coupled to a rotary drive 22 that is rotatably coupled to a tip 23. A suction port 24 in the casing 20 is used for applying the negative pressure inside the handpiece 15 and for the evacuation of waste into the separation container 14. A supply port 25 in the casing 20 is used to supply solution under pressure from the pumping unit 16 to the tip 23. The tip 23 comprises two assembled parts which form the unit with two channels. An external channel 26 is used to supply the cosmetic or medical solution under pressure via the supply port 25 to one or more nozzles 27 positioned in the distal part of the tip 23, which contact the skin surface. The nozzles 27 face toward the longitudinal axis of the tip 23 and perpendicular to its inside surface. An internal channel 28 of the tip 23 is designated for the waste evacuation via the suction port 24 and for gripping the treated skin area.

Figure 3A:
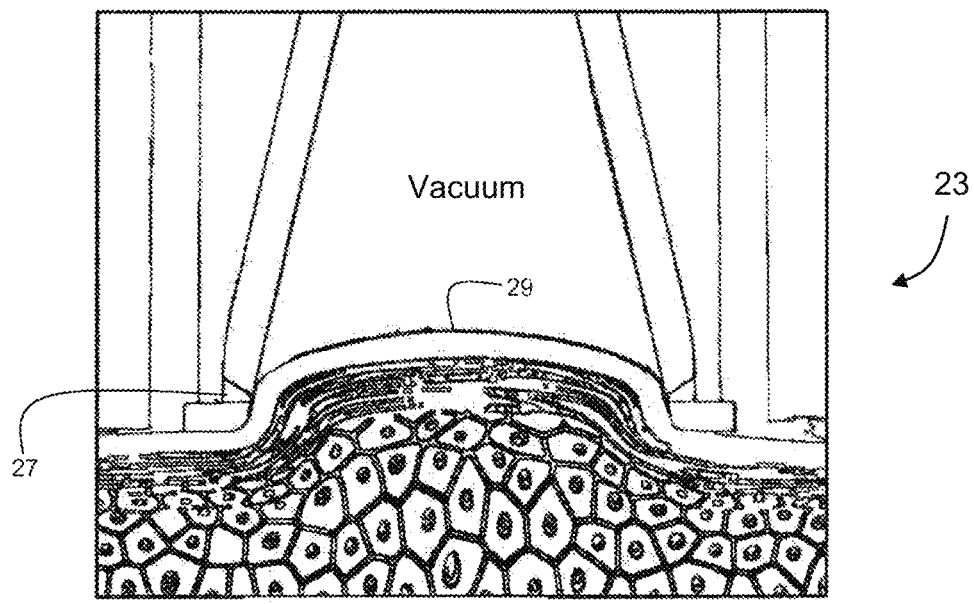
FIGS. 3a and 3b are enlarged schematic drawings showing a detail of the handpiece during delivery of medicine or cosmetic via human skin pores.

The operation of the system 10 illustrated in Figure 1a will now be described. First the compressor 11 is activated, which applies air under high pressure to the ejector 12. The ejector 12 generates negative pressure, i.e., suction, in the separation container 14 and the handpiece 15. When the distal part of the tip 23 of the handpiece 15 contacts the skin surface, limited deformation of the skin region 29 within the perimeter of the tip 23 occurs. Owing to the negative pressure, the skin is drawn into the open chamber 28 of the tip 23 to a level that overlaps the nozzles 27 and is seated along the internal contour of the tip 23, thereby adopting its shape 29 along the points of contact as shown in FIG. 3a. The pumping unit 16 is then activated which supplies the liquid under pressure to the handpiece 15 via the supply port 25 from the storage container 17. At the same time, the motor 21 is activated and starts to rotate the tip 23 via the rotary drive 22. The medical or cosmetic solution ejected by the nozzles 27 of the rotating tip 23 flow to the skin surface 29 (shown in FIGS. 3a and 3b) located inside the open chamber 28 of the tip 23.

Figure 3B:
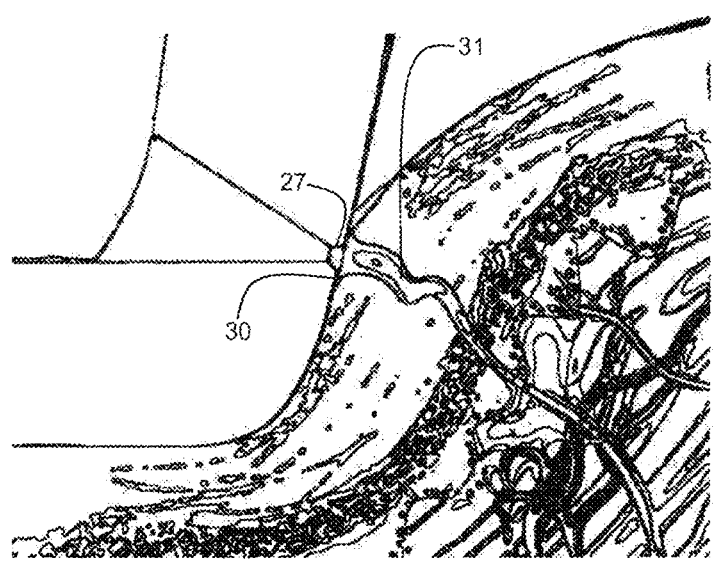

A jet of the medical or cosmetic solution under pressure (of about 1-2 bar) is delivered via the nozzles 27 and circulates over the deformed skin region (shown in FIG. 3a) during rotating contact of the tip 23. At the moments when, as shown in FIG. 3b, the outlet of a nozzle 27 in the tip 23 is located wholly within an inlet 30 of a pore, sluicing occurs, whereby the channel of the nozzle 27 is momentarily connected to the pore channel 31. Since the exit diameter of the nozzles 27 is smaller than that of the pore inlet 30, the liquid jet permeates into the pore interior without any resistance. Thus, during coincidence of the nozzles 27 and the pore inlet 30, the pore channel 31 is filled with the medical or cosmetic solution.

Pores contain structured hydrophilic and lipophilic domains with unilateral conductivity only toward the outside. However they are not protected against propagation of a single jet of solution flowing centrally toward the channel depth. During coincidence between the nozzle and the pore inlet, the pore channel is filled with a certain amount of the liquid. The pore channel 31 continues filling as long as the moving nozzles 27 of the tip 23 and the pore inlets 30 remain coincident. The amount of liquid permeating into the pores depends on the difference between the size of the solution delivery nozzle 27 and that of the pore inlets 30, i.e. as the pore size increases so too does the sluicing time with the nozzle. On the other hand the faster the tip rotation velocity, the shorter the sluicing duration. As the pressure of the medical or other solution rises, the quantity of liquid entering the pore increases. When motion of the orifice of the nozzle 27 overlaying the pores inlet 8 is arrested, the stretched throat of the pore contracts and encapsulates the residual solution in the pore channel 31. Treatment is performed by moving the handpiece 15 over the skin surface. When used medically, it has been demonstrated experimentally that a tip 23 with an outer diameter of 5 mm with a nozzle diameter of 50 µm provided the best medical effect. The optimal rotation velocity of the tip 23 was found to be 160 revolutions per minute (RPM) with a solution pressure of 1-6 bars. According to some examples, the rotational velocity for certain applications may be different, for example up to 200 RPM.

The average liquid volume permeating inside an individual pore depends on jet pressure, the rotation velocity of the tip 23 and its geometry, and should reach 0.05-0.3 mm$^3$. The maximum estimated amount of liquid spread over all the affected skin appendages is about 2 ml/200 cm$^2$.

For example in the case of an aesthetic procedure, the delivery of mild Alpha Hydroxy Acids (2-5%) via the pores extends to the depth of the dermis without damaging the skin. Usually this is possible only if skin integrity has been disrupted, i.e. the epidermis and dermis are damaged. In response to what appears as a threat, namely penetration of foreign solutions into the skin, the immune and nervous systems activate to repair potential damage from what is perceived as possible irritant penetration inside the skin. Thus, a real inflammatory response is generated by the extremely mild irritants that have permeated through the pores. The body's natural immune and infection protection systems promptly go into action to heal the non-existent damage to the skin.

As a result cell multiplication rate is increased and new epidermis cells are generated. The gross factors responsible for natural collagen production are activated in the dermis.

The method in the aesthetic application case, cosmetic solution delivery via pores under pressure, causes thickening of the dermis. Production of additional natural collagen improves skin density and causes smoothing of small wrinkles. As a result of sufficiently deep penetration into the dermis, a process of neurocosmetic and regenerative effect on the skin is steadily developed and persists for months. The delivery of non-damaging solutions via pores enables all the natural functions of skin protection and interaction with the environment.

Operation of the system 110 as described above with reference to FIG. 1b is similar to the operation of the system 10 of FIG. 1a, with the addition of an application of an electrical current to the patient and the liquid delivered by the system 110. In order to accomplish this, the electrode 18 is brought into contact with the patient's skin, for example by having the patient grasp it or by fastening it around a part of his body, such as the wrist, finger, etc. Thus, the patient is connected to, e.g., the positive terminal of the power source 18b. An electrical current is thereby imparted to the skin, in particular in the vicinity of the pores. The current may be about 0.25 mA. As the diameter of the stream is about 50 µm, the current density is about 13 A/cm$^2$. This difference in charge between the patient's skin and the liquid dispensed via the handpiece facilitates delivery of the liquid through the pores.

Figure 4:
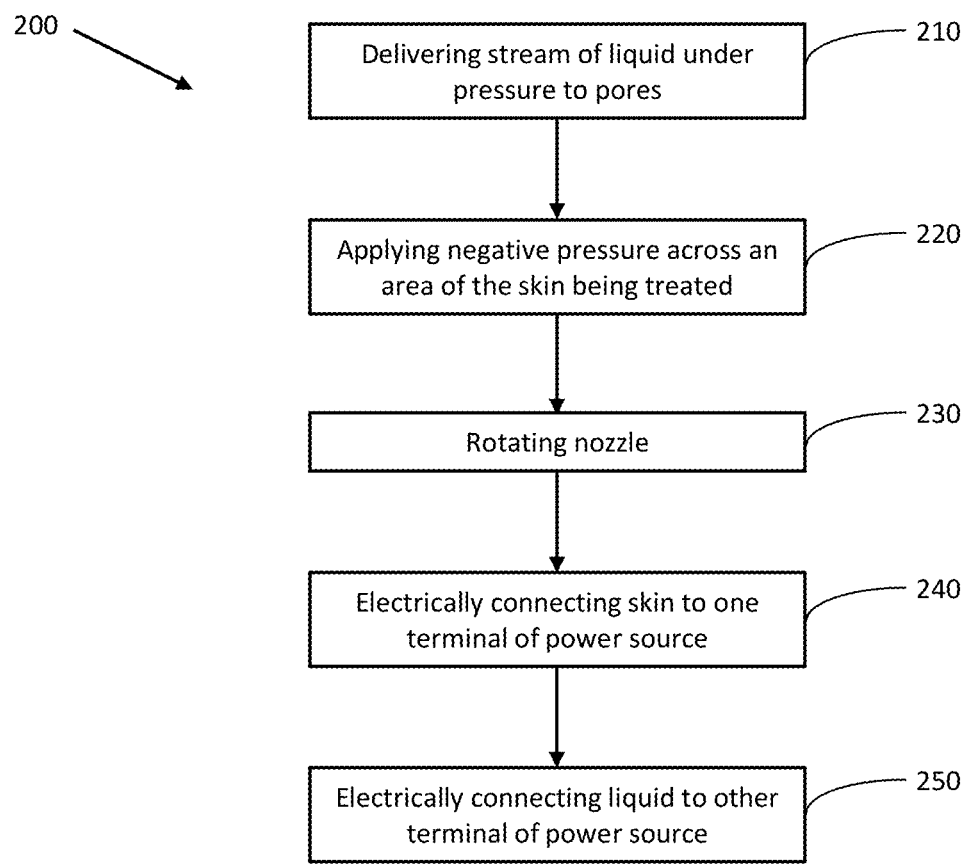
FIG. 4 illustrates a method of delivering liquid into the pores of recipient human skin which may be carried out with the system illustrated in FIG. 1b.

As illustrated in FIG. 4, the system 110 may be used in a method 200 to deliver the liquid into the pores of recipient human skin. In step 210, a stream of the liquid is delivered to the pores under pressure. The stream may have a cross-section which, at its widest point, is smaller than an inlet opening of the pore. For example, the cross-section may have a diameter which is no greater than about 50 µm.

In step 220, a negative pressure is applied across the area of the skin being treated.

In step 230, the nozzle via which the stream is delivered is rotated. The speed of the rotation may be up to about 200 RPM. According to some examples, it is between about 160 RPM and 200 RPM.

In step 240, the skin is electrically connected to one terminal of the power source 18b, for example via the electrode 18.

In step 250, the liquid is electrically connected to the other terminal of the power source 18b. This imparts an electrical current to the skin in the vicinity of the pores. This current may be in the range of about 0.2 mA to 0.3 mA.

It will be appreciated that some of the steps of the method, for example applying a negative pressure (step 220) and/or rotating the nozzle (step 230) may be optional.

It will be further appreciated that all steps of the method mat be carried out simultaneously, e.g., such that the delivering of the liquid happens at the same time that the negative pressure is applied, the nozzle is rotated, and the terminals of the power source 18b are connected to the skin and/or liquid.

It is to be understood that while the invention has been described with particular regard to the injection of a medicinal solution through the pores of a human patient, it is equally applicable to the injection of non-medical solutions such as cosmetics in non-therapeutic treatment of the human body.

It is also to be understood that typically the nozzles are circular in cross-section, such that the nozzle diameter is less than the inlet size of the pores. However, the nozzles need not be circular in cross-section provided that their outlet produces a stream whose cross-section at its widest point is smaller than the narrowest point in the inlet opening of a human skin pore.

Those skilled in the art to which this invention pertains will readily appreciate that numerous changes, variations and modifications can be made without departing from the scope of the invention mutatis mutandis.

What is claimed is:

1. A non-invasive system for delivering a liquid onto a depth of a dermis under a stratum corneum via pores of a human's skin, the system comprising:
    a storage container for containing said liquid;
    a pumping unit coupled to the storage container for increasing a pressure of said liquid;
    a suction mechanism configured to generate a negative pressure, said suction mechanism comprising:
        a separation container for providing liquid separation of a liquid-gas mixture;
        a compressor;
        a gas ejector connected to said compressor;
        a connecting tube between said separation container and said gas ejector;
    an operating handpiece comprising:
        a motor;
        a rotary drive coupled said motor;
        a tip rotatably coupled to said rotary drive, said tip comprising:
            an open chamber, and
            an external channel;
        an outer casing accommodating said motor and said rotary drive, and further including:
            at least one suction port for applying negative pressure inside said open chamber, and at least one supply port for supplying said liquid into said external channel under pressure from said pumping unit;

a power source having a first terminal and a second terminal of opposite charges;

an electrode connected to the first terminal of said power source and being configured for being brought into contact with the human skin during a delivery; and an electrical connection between said second terminal of said power source and the liquid within the external channel of the handpiece;

wherein the tip of said operating handpiece comprises at least one nozzle for delivery of the liquid from said external channel directly into a pore of the human skin drawn into the open chamber; and wherein said nozzle comprises an outlet having a diameter smaller than an opening of said pore such that said nozzle delivers a stream having a cross-section smaller than an inlet of said pore, such that the liquid in electrical contact with the second terminal of the power source completes an electric circuit through the skin to the electrode connected to the first terminal of the power source.

2. The system according to claim 1, wherein a diameter of the cross-section of said stream is no greater than about 50 μm.

3. The system according to claim 1, wherein said tip is configured to rotate at a speed greater than about 160 revolutions per minute.

4. The system according to claim 3, wherein said tip is configured to rotate at a speed no greater than about 200 revolutions per minute.

5. The system according to claim 1, wherein said at least one suction port is connected to said suction mechanism via an open chamber of the tip configured for applying negative pressure via the tip of the handpiece across an area of skin being treated.

* * * * *